United States Patent
Banckwitz et al.

(10) Patent No.: US 8,213,574 B2
(45) Date of Patent: Jul. 3, 2012

(54) METHOD FOR OPERATING AN X-RAY IMAGE RECORDING DEVICE HAVING A MOVEABLE X-RAY DETECTOR ON THE X-RAY C-ARM

(75) Inventors: Rosemarie Banckwitz, Forchheim (DE); Philipp Bernhardt, Forchheim (DE); Johannes Rieber, München (DE)

(73) Assignee: Siemens Aktiengesellschaft, München (DE)

( * ) Notice: Subject to any disclaimer, the term of this patent is extended or adjusted under 35 U.S.C. 154(b) by 182 days.

(21) Appl. No.: 12/836,653

(22) Filed: Jul. 15, 2010

(65) Prior Publication Data

US 2011/0013747 A1    Jan. 20, 2011

(30) Foreign Application Priority Data

Jul. 17, 2009    (DE) .......................... 10 2009 033 675

(51) Int. Cl.
 *H05G 1/64*    (2006.01)
(52) U.S. Cl. .......................................................... 378/98
(58) Field of Classification Search .................... 378/19, 378/98, 62, 205, 163, 196, 206
See application file for complete search history.

(56) References Cited

U.S. PATENT DOCUMENTS

| | | | |
|---|---|---|---|
| 7,194,065 B1 * | 3/2007 | Boutenko et al. | 378/108 |
| 2002/0012420 A1 * | 1/2002 | Bani-Hashemi et al. | 378/63 |
| 2004/0254456 A1 * | 12/2004 | Ritter | 600/425 |
| 2009/0028291 A1 * | 1/2009 | Graumann | 378/19 |

FOREIGN PATENT DOCUMENTS

| | | |
|---|---|---|
| DE | 10345509 A1 | 5/2005 |
| DE | 102005006895 A1 | 8/2006 |
| DE | 102007021770 A1 | 11/2008 |

OTHER PUBLICATIONS

Philipp Bernhardt, Lothar Bätz, Ernst-Peter Rührnschopf, Martin Hoheisel, "Spatial Frequency-Dependent Signal-to-Noise Ratio as a Generalized Measure of Image Quality", Medical Imaging 2005: Physics of Medical Imaging, edited by Michael.J. Flynn, Proceedings of SPIE vol. 5745, pp. 407-418 (SPIE, Bellingham, WA, 2005); Others; 2005.

Clarence L. Gordon, "Image quality optimization using an x-ray spectra model-based optimization method", Proc. SPIE vol. 3977, pp. 456-465, Medical Imaging 2000: Physics of Medical Imaging, James T. Dobbins; John M. Boone; Eds.; Others; 2000.

* cited by examiner

*Primary Examiner* — Irakli Kiknadze

(57) ABSTRACT

A method for operating an x-ray image recording device having a movable x-ray detector on an-x-ray c-arm is provided. The x-ray C-arm supports an x-ray source and the x-ray detector which can be moved in the direction of the x-ray source. A variable is calculated which specifies the image quality of an x-ray image to be obtained in a position of the x-ray C-arm in a position of the x-ray detector and/or specifies the exposure dose of an operating person. A measure is taken as a function of the variable which results in a movement of the x-ray detector by the operating person and/or by an automatic movement. X-ray images are recorded in positions of the x-ray detector in which the image quality and/or the exposure dose of an operating person are optimal.

20 Claims, 1 Drawing Sheet

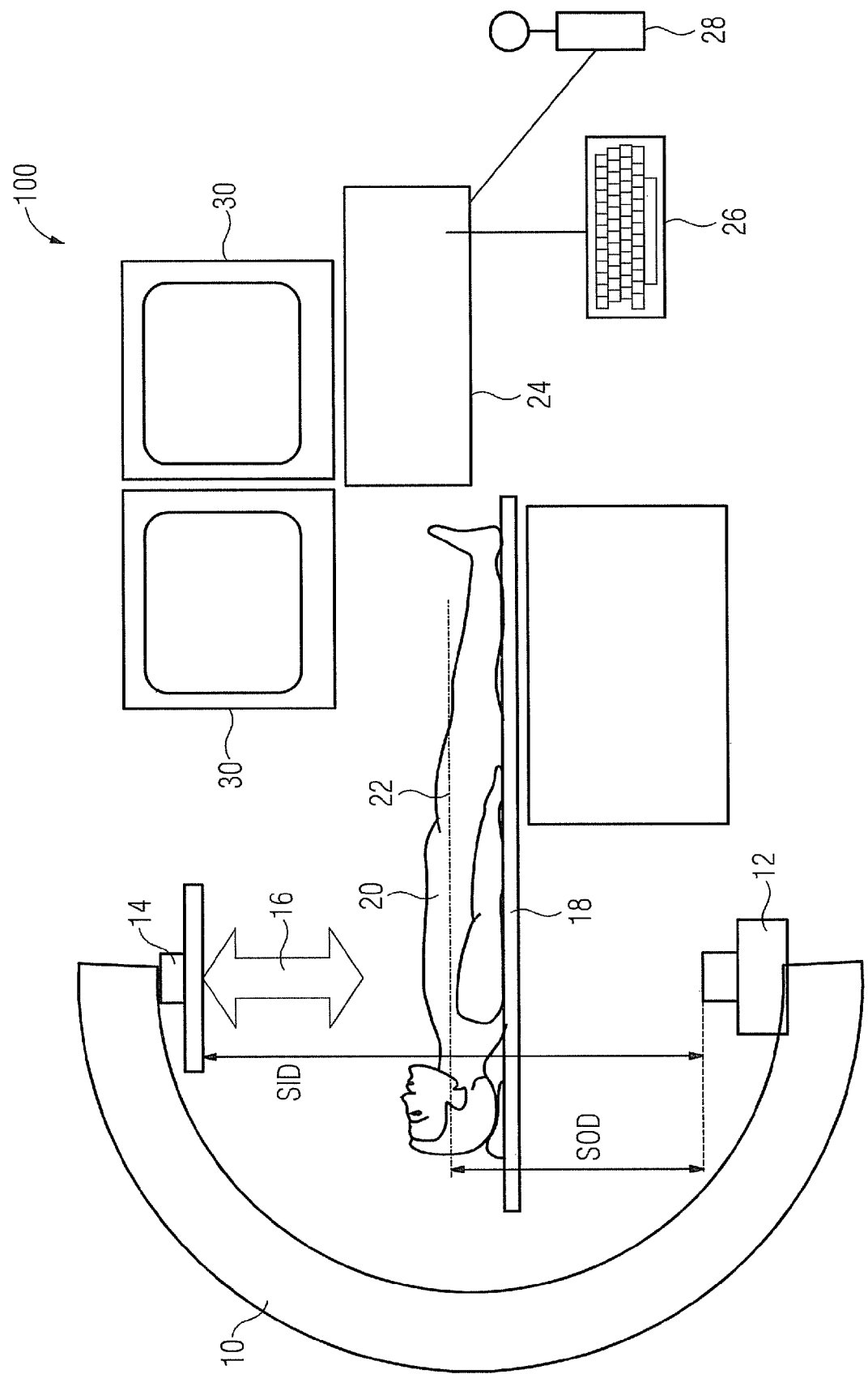

METHOD FOR OPERATING AN X-RAY IMAGE RECORDING DEVICE HAVING A MOVEABLE X-RAY DETECTOR ON THE X-RAY C-ARM

CROSS REFERENCE TO RELATED APPLICATIONS

This application claims priority of German application No. 10 2009 033 675.3 filed Jul. 17, 2009, which is incorporated by reference herein in its entirety.

FIELD OF THE INVENTION

The invention relates to a method for operating an x-ray image recording device. It is assumed that this comprises a moveable x-ray C-arm, which supports an x-ray source and an x-ray detector. This is the case with x-ray angiography devices for instance. The x-ray C-arm can typically be twisted and tilted about an axis of rotation as a whole. It is also assumed here that the x-ray detector can be moveable on its part opposite to the x-ray C-arm, namely such that its distance from the x-ray source can be changed as a result. This is also regularly the case with many newer x-ray image recording devices, in particular x-ray angiography devices.

BACKGROUND OF THE INVENTION

Flat-panel detectors are used in modern x-ray image recording devices of this type. Over the years, these have replaced the previously used image amplification systems. With these earlier image amplification systems, it was necessary to keep the distance between the patient and the image amplifier as minimal as possible, since the radiation dose needed to achieve an adequate image increases quadratically with the distance of the image amplifier from the x-ray source. In terms of the number of impacting photons, as small a distance as possible between the patient and the flat panel detector would also be advantageous with the use of flat panel detectors. The operating personnel, particularly if he/she has learnt to operate the x-ray image recording devices on such with the image amplification systems, still tend to select such settings, whereby the distance between the patient and the flat panel detector is as small as possible.

The question arises as to whether an optimal image quality is always achieved. Furthermore, the exposure dose of an operating person by means of scatter radiation, which was previously absorbed in the detector, is also to be minimized.

SUMMARY OF THE INVENTION

It is the object of the present invention to indicate a way in which the operation of an x-ray image recording device can achieve a good image quality or the dose exposure for the treating personnel can be kept minimal.

The object is achieved by a method having the features according to the claims. Accordingly, at least one user input for moving the x-ray C-arm into a predetermined position is initially received by the x-ray image recording device. Subsequently, the x-ray C-arm is moved into the predetermined position by means of the x-ray image recording system. While no attention is now paid in the prior art to a maneuverability of the x-ray detector and/or if need be inputs for moving the same are received with no response thereto, a variable specifying (in other words containing and/or considering) the image quality of an x-ray image to be obtained in this position and/or specifying the exposure dose of an operating person is determined in accordance with the invention at at least one relative position between the x-ray source and x-ray detector in the predetermined position of the x-ray C-arm. As a function of the thus determined at least one variable, a measure is taken by the x-ray image recording device to effect a movement of the x-ray detector.

The invention relates to the knowledge that the distance between the x-ray source and x-ray detector has an effect on the image quality and also on the exposure dose of an operating person. To this end, a quantitative statement can be made, which can be more or less accurate and/or detailed. As a result of the quantitative statement, a decision can then be made to determine whether or not the position of the x-ray detector provided without further measures is acceptable. In the latter case, the measure is then taken to effect a movement.

The quantification of the image quality can take the entire radiation path into account.

This thus starts in that the x-ray radiation source differs from a point source. The influence of the deviation of the x-ray source from a point source can then be taken into account in one factor. The larger the path, across which the x-ray radiation is focused, the more a blurring affects the focus. A radiation profile (the so-called focal spot) can be determined from the x-ray radiation. This profile can be subjected to a Fourier transformation and provided the Fourier transformations are standardized such that the value of one is achieved with a frequency of zero, a factor can be immediately determined which can be taken into account in the variable.

The x-ray source follows the image object in the radiation path. Depending on the distance of the x-ray detector from the x-ray source and thus also from the image object, if the x-ray detector is moved, the portion of scatter radiation reaching the x-ray detector can change. This can be easily explained in that starting from any point in the image object, the x-ray radiation detector lies at a smaller spatial angle with an increasing distance from the image object so that less scatter radiation reaches the x-ray detector. The factor can in particular be removed from tables or determined on the basis of a numerical simulation.

The x-ray radiation finally reaches the x-ray detector and a factor, which takes the performance of the same into account, can also be taken into account in the variable. The performance is determined by the production of x-ray quanta, on the other hand also by the ratio of the object size relative to pixel size. Both effects can be taken into account in a single factor, which can be referred to as "detective quantum efficiency".

If three factors are taken into consideration in the variable and the exposure dose of an operating person is neglected, this variable is nothing other than the signal-to-noise ratio in an x-ray image, which has been obtained with the predetermined position of the x-ray C-arm and the position of the x-ray radiation detector, at which the variable is determined. The signal-to-noise ratio is herewith specified as a function of the spatial frequencies in the space of an image object.

Aside from the position of the x-ray C-arm, other influencing factors may also determine the image quality, namely in a manner which differs for different distances of the x-ray detector from the x-ray radiation source. In a preferred embodiment, at least one further input for determining conditions is therefore received during the exposure and this takes into account at least one further input during determination of the variable. The input enables the thickness and condition of the radiated object to be specified for instance, the height of the patient table, on which the patient rests as an image object, a pulse rate for the x-ray radiation, and the dose rate effected by the x-ray radiation inter alia are specified. All of this can be taken into account during determination of the variable.

With a particularly simple embodiment, which is therefore computationally uncomplicated, the variable is only determined at a current position of the x-ray C-arm and is compared with a threshold value. The term "current position" refers to the position which is assumed after receiving the inputs by means of the operating person, be it that the operating person has intentionally moved the x-ray detector, be it that its relative position from the x-ray source has not changed at all and has left the already adjusted relative position. The comparison with a threshold value can then decide whether or not a measure is taken to effect a movement of the x-ray detector. Depending on the definition of the variable, such a threshold value can be exceeded or not reached so that such a measure is taken. This embodiment can herewith be configured in a particularly effortless fashion, if a measure, with a predetermined output of the comparison with the threshold value (namely when not reaching or exceeding, depending on the definition of the variable), outputs a warning signal to an operating person. Such a warning signal informs the operating person that an excessively poor image quality is achieved with the current position of the x-ray detector in respect of the x-ray C-arm, if necessary the exposure dose of an operating person is too high. The operating person can then move the x-ray radiation detector him/herself. If necessary, the variable can then be determined once again, with which the threshold value is compared until the warning signal is no longer output.

If the method is to work particularly precisely and a particularly high image quality of a spatial image is to be achieved, the variable is determined at a plurality of positions of the x-ray detector in respect of the x-ray C-arm, and the position in which the image quality of an x-ray image, which is recorded in this position, is at its best. To some extent, a curve progression is obtained relative to the variable as a function of a moving parameter for the x-ray detector and can then determine the position, in which the curve has a maximum (and/or in another definition, a minimum).

If the optimal position is determined, an output to an operating person can take place, by way of which the same is reported. It is then left to the operating person to adopt this position. In fact, this method is only successful if the operating person is adequately skilled and attentive, less effort is needed in return.

It is alternatively possible for the x-ray detector to be automatically (in other words mechanically by means of the x-ray image recording device) moved into the best position, in which according to a specific criterion the variable is at its best for instance, the image quality is at its best, and the signal-to-noise ratio has a maximum for instance.

In order not to deprive the operator of control as a result of the measure for effecting a movement of the x-ray detector and such a movement of the x-ray detector which is introduced in this way, provision can be made for an enlargement to be determined with an initially assumed position of the x-ray C-arm, namely with such a position which is assumed as a result of control commands from an operating person and/or remains unchanged. After moving the x-ray detector as a result of the effected measure, recorded x-ray images can then be post-processed, namely such that an image is shown with the previously determined enlargement. If the operating person has selected or intentionally left the position of the x-ray detector such that a completely determined enlargement is achieved, the enlargement is not changed by moving the x-ray detector, as a result of which the acceptance of the inventive method can be increased.

BRIEF DESCRIPTION OF THE DRAWINGS

A preferred embodiment of the invention is described below with reference to the drawing, in which, the sole FIGURE shows a schematic representation of an x-ray image recording system and/or device, namely an x-ray angiography device, with which the inventive method can be implemented.

DETAILED DESCRIPTION OF THE INVENTION

An x-ray angiography device which is referred to overall with 100 has an x-ray C-arm 10. This can, as a whole, be rotated, in a manner known per se, and tilted about an axis of rotation. The x-ray C-arm 10 supports an x-ray source 12 and an x-ray detector 14. The x-ray detector 14 can be moved to and fro opposite the x-ray C-arm 10 in the direction of the x-ray source 12, see the double arrow 16 indicating the maneuverability. A patient table 18, on which a patient 20 is located, is shown here. An image plane 22 is defined relative to the patient 20. The distance of this image plane 22 from the x-ray source 12 is referred to as SOD, the distance between the x-ray source 12 and the x-ray detector 14 is referred to as SID. This latter distance SID can change by moving the x-ray detector 14, and thus also the distance between the x-ray detector 14 and the image plane 22, SID-SOD.

The x-ray angiography device comprises a data processing facility 24, which can be operated by way of input means 26 and 28. By way of example, a keyboard and a control billet are shown as an input means 26 and 28 respectively. It is possible to show the inputs of an operating person on the monitor 30. Subsequently recorded x-ray images can similarly be displayed on this monitor 30.

It is assumed here that in the presence of a patient 20 lying on the patient table 18, an operating person has moved the x-ray C-arm 10 into a predetermined position by means of the input facilities 26 and/or 28, namely into the position shown here. If necessary, he/she has also moved the x-ray detector 14. Furthermore, the operating person has executed inputs, by way of which the conditions of the generation of an x-ray image are input, e.g. the x-ray dose (if necessary by way of a voltage applied to the x-ray source 12). In addition to the angulation and rotation of the x-ray C-arm, he/she may have adjusted the table height of the table 18 and have determined the pulse rate for the generation of x-ray images. Once all these inputs have been completed, the calculation of the signal-to-noise ration SNR(u,v) is introduced, with u,v noise frequencies in the image plane 22. The signal to noise ratio SNR(u,v) is calculated for a plurality of positions of the x-ray detector 14 in which it can be moved in accordance with arrow 16, for instance for a plurality of distances SID.

Three components are taken into consideration here.

The so-called focal spot intensification is initially taken into consideration:

The x-ray radiation emitted by the x-ray source 12 can be described by a focal spot in the focal plane. This focal spot has a profile which is determined by the expansion of the x-ray source 12. This profile can now be subjected to a Fourier transformation and standardized such that with values of u=v=0, the Fourier transformation has a value equal to one. This Fourier transformation is referred to as MTF (u,v) so that:

$SNR(u,v) \sim MTF(u*\gamma/\gamma-1, v*\gamma/\gamma-1) = f_1$ applies. $\gamma$ is herewith the enlargement factor, SID divided by SOD. The adjustment in the argument of the function accordingly takes place because the variable SNR (u,v) applies to an x-ray image obtained on the x-ray detector 14, so that the enlargement factor is taken into account.

To calculate SNR (u,v), the scatter radiation must also be taken into account, in other words radiation which is scattered in the patient 20 and accordingly reaches the x-ray detector 14. There is no formula for this dependency. It can be simulated numerically or measured in advance and then tabulated in a memory of the data processing facility 24. A further factor $f_2$ is obtained, whereby SNR (u,v)~$f_2$.

Finally, the so-called detector performance of the x-ray detector 14 must also be taken into consideration. In this case, electrical noise results if the number of x-ray quanta, which strike the x-ray detector, is minimal: Only individual x-ray quanta strike the individual detector elements, which correspond to image elements (pixels) of an x-ray image. The detector performance is also dependent on the spatial frequency, particularly once the spatial frequency achieves the variable of the detector elements: objects, which are barely larger than the individual elements, can namely be poorly imaged. A further $f_3$ can therefore be determined, with SNR (u,v)~DQE (u$\gamma$,v$\gamma$)=$f_3$. The reference "DQE" stands here for the "Detective Quantum Efficiency", in which both the electrical noise and also the frequency dependency are taken into consideration.

The signal to noise ratio SNR (u, v) can thus be calculated by:

$$SNR(u,v)=c*f_1*f_2*f_3, \text{ whereby } c \text{ is a proportional factor.}$$

The afore-cited formula dependencies are already described as such in an article, namely in the article "Spatial Frequency-Dependent Signal-to-Noise Ratio as a Generalized Measure of Image Quality" by Philip Bernhardt, Lothar Bätz, Ernst-Peter Rührnschopf, Martin Hoheisel, which was published in Medical Imaging 2005: Physics of Medical Imaging; edited by Flynn, Michael J.; Proceedings of the SPIE, Vol. 5745, pages 407-418 in 2005 and its contents are included in the present application as reference insofar as possible for the prevalent patent law.

The signal-to-noise ratio SNR (u, v) is now cited as above for a plurality of positions of the x-ray detector 14, so that a curve of SNR (u, v) is obtained as a function of SID and/or a moving parameter. This curve has a maximum. The distance SID, in which the maximum prevails, is therefore the distance at which the image quality is at its best.

Because the x-ray angiography device 100 has determined this best distance SID by means of its data processing facility 24, it automatically effects a movement of the x-ray detector 14 such that this distance is assumed. Alternatively, an operator can be notified on the monitor 30 how far the x-ray detector 14 is to be moved. Furthermore, a warning signal can alternatively only be output if the current position of the x-ray detector 14 is particularly unfavorable, e.g. the variable SNR (u,v) deviates by a predetermined value or percentage rate from the best value.

In addition or alternatively to using the signal-to-noise ratio SNR(u,v), it is also possible to determine the extent of the exposure dose to an operating person, this likewise being dependent on the position of the x-ray radiation detector 14. A second variable can be determined and an algorithm can be defined, in which the two variables are to be weighted and taken into account in order to find an optimal distance SID. The data processing facility 24 can determine, before effecting the movement of the x-ray detector 14, how the enlargement $\gamma$ is and, after moving the x-ray detector 14, scale recorded x-ray images such that x-ray images with an enlargement $\gamma$ are shown on the monitor 30.

The invention claimed is:

1. A method for operating an x-ray image recording device having a moveable x-ray C-arm, comprising:
   receiving a user input for moving the x-ray C-arm into a predetermined position by the x-ray image recording device;
   moving the x-ray C-arm into the predetermined position, the x-ray C-arm supporting an x-ray source and an x-ray detector, and the x-ray detector being moveable opposite to the x-ray C-arm for changing a distance from the x-ray source;
   determining a variable at a relative position between the x-ray source and the x-ray detector in the predetermined position, the variable specifying an image quality of an x-ray image to be obtained by the x-ray image recording device in the predetermined position and/or specifying an exposure dose of an operating person when recording the x-ray image; and
   taking a measurement for effecting a movement of the x-ray detector by the x-ray image recording device based on the variable.

2. The method as claimed in claim 1, wherein the variable is determined by a factor comprising:
   an influence of a deviation of the x-ray source from a point source,
   an influence of a scatter radiation reaching the x-ray detector from an image object, or
   a performance of the x-ray detector.

3. The method as claimed in claim 1, wherein the variable is a signal-to-noise ratio in the x-ray image specified in an image object as a function of spatial frequencies.

4. The method as claimed in claim 1, wherein an input for determining a condition when recording the x-ray image is received by the image recording device and the condition is included in the determination of the variable.

5. The method as claimed in claim 1, wherein the variable is determined at a current position of the x-ray detector relative to the x-ray C-arm and is compared with a threshold value.

6. The method as claimed in claim 5, wherein a warning signal is output to the operating person if the variable exceeds the threshold value.

7. The method as claimed in claim 1,
   wherein the variable is determined at a plurality of positions of the x-ray detector relative to the x-ray C-arm, and
   wherein a best position of the x-ray detector is determined from the plurality of positions at which the variable is at a best value based on a predetermined criterion.

8. The method as claimed in claim 7, wherein a signal is output to the operating person when the x-ray detector is at the best position.

9. The method as claimed in claim 7, wherein the x-ray detector is automatically moved into the best position.

10. The method as claimed in claim 1,
    wherein an enlargement factor is determined at a first position of the x-ray detector relative to the x-ray C-arm, and
    wherein the x-ray image recorded with the enlargement factor is postprocessed after moving the x-ray detector.

11. An x-ray image recording device, comprising:
    an x-ray source;
    an x-ray detector;

a moveable x-ray C-arm that supports the x-ray source and the x-ray detector, the x-ray detector being moveable opposite to the x-ray C-arm to change a distance from the x-ray source;

an input device that receives a user input for moving the x-ray C-arm into a predetermined position; and a data processing device that determines a variable at a relative position between the x-ray source and the x-ray detector in the predetermined position, the variable specifying an image quality of an x-ray image to be obtained by the x-ray image recording device in the predetermined position and/or specifying an exposure dose of an operating person when recording the x-ray image, wherein the x-ray image recording device is configured to take a measurement for effecting a movement of the x-ray detector based on the variable.

12. The device as claimed in claim 11, wherein the variable is determined by a factor comprising:

an influence of a deviation of the x-ray source from a point source, an influence of a scatter radiation reaching the x-ray detector from an image object, or a performance of the x-ray detector.

13. The device as claimed in claim 11, wherein the variable is a signal-to-noise ratio in the x-ray image specified in an image object as a function of spatial frequencies.

14. The device as claimed in claim 11, wherein an input for determining a condition when recording the x-ray image is received by the image recording device and the condition is included in the determination of the variable.

15. The device as claimed in claim 11, wherein the variable is determined at a current position of the x-ray detector relative to the x-ray C-arm and is compared with a threshold value.

16. The device as claimed in claim 15, wherein a warning signal is output to the operating person if the variable exceeds the threshold value.

17. The device as claimed in claim 11, wherein the variable is determined at a plurality of positions of the x-ray detector relative to the x-ray C-arm, and wherein a best position of the x-ray detector is determined from the plurality of positions at which the variable is at a best value based on a predetermined criterion.

18. The device as claimed in claim 17, wherein a signal is output to the operating person when the x-ray detector is at the best position.

19. The device as claimed in claim 17, wherein the x-ray detector is automatically moved into the best position.

20. The device as claimed in claim 11, wherein an enlargement factor is determined at a first position of the x-ray detector relative to the x-ray C-arm, and wherein the x-ray image recorded with the enlargement factor is postprocessed after moving the x-ray detector.

* * * * *